US 9,902,028 B2

(12) United States Patent
Amsler

(10) Patent No.: US 9,902,028 B2
(45) Date of Patent: Feb. 27, 2018

(54) EXTERNAL CASE FOR A WEARABLE MEDICAL DEVICE

(71) Applicant: Zoll Medical Corporation, Chelmsford, MA (US)

(72) Inventor: Phillip Amsler, Oakmont, PA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 89 days.

(21) Appl. No.: 14/945,511

(22) Filed: Nov. 19, 2015

(65) Prior Publication Data

US 2016/0166321 A1    Jun. 16, 2016

Related U.S. Application Data

(60) Provisional application No. 62/082,365, filed on Nov. 20, 2014.

(51) Int. Cl.
| | | |
|---|---|---|
| *A61N 1/00* | (2006.01) | |
| *B23P 19/04* | (2006.01) | |
| *A61N 1/39* | (2006.01) | |
| *A61B 19/02* | (2006.01) | |
| *A61B 50/31* | (2016.01) | |
| *A61B 50/30* | (2016.01) | |

(52) U.S. Cl.
CPC .............. *B23P 19/04* (2013.01); *A61N 1/39* (2013.01); *A61N 1/3968* (2013.01); *A61B 2019/0221* (2013.01); *A61B 2019/0239* (2013.01); *A61B 2050/301* (2016.02); *A61B 2050/3011* (2016.02); *A61B 2050/311* (2016.02)

(58) Field of Classification Search
CPC ................................ A61N 1/39; A61N 1/3968
USPC ............................................................. 607/5
See application file for complete search history.

(56) References Cited

U.S. PATENT DOCUMENTS

| | | |
|---|---|---|
| D269,373 S | 6/1983 | Belt et al. |
| 4,928,690 A | 5/1990 | Heilman et al. |
| 5,078,134 A | 1/1992 | Heilman et al. |
| D343,901 S | 2/1994 | Anderson |
| 5,741,306 A | 4/1998 | Glegyak et al. |
| 5,944,669 A | 8/1999 | Kaib |
| 6,065,154 A | 5/2000 | Hulings et al. |
| 6,253,099 B1 | 6/2001 | Oskin et al. |
| 6,280,461 B1 | 8/2001 | Glegyak et al. |
| 6,422,669 B1 | 7/2002 | Salvatori et al. |
| 6,681,003 B2 | 1/2004 | Linder et al. |
| D494,681 S | 8/2004 | Mills et al. |
| D548,346 S | 8/2007 | Vaisnys et al. |
| D597,211 S | 7/2009 | Ewing et al. |
| D616,993 S | 6/2010 | Muis et al. |
| D643,618 S | 8/2011 | Guichet |
| D659,836 S | 5/2012 | Bensch et al. |

(Continued)

*Primary Examiner* — Nadia A Mahmood
(74) *Attorney, Agent, or Firm* — The Webb Law Firm

(57) ABSTRACT

A case for a wearable medical device is provided. The wearable medical device includes internal circuitry enclosed within an external housing. The case includes a first part sized to surround a first portion of the external housing and a second part sized to surround a second portion of the external housing. The first part includes an inner surface with contours configured to receive corresponding contours of the external housing. The first part is connected to the second to form a parting line around the external housing. An assembly including a wearable medical device and an external case is also provided.

39 Claims, 12 Drawing Sheets

(56) References Cited

U.S. PATENT DOCUMENTS

| | | |
|---|---|---|
| 8,271,082 B2 | 9/2012 | Donnelly et al. |
| D668,037 S | 10/2012 | London |
| D676,134 S | 2/2013 | Saevareid et al. |
| 8,369,944 B2 | 2/2013 | Macho et al. |
| D690,818 S | 10/2013 | Pastrick et al. |
| D699,430 S | 2/2014 | Kantor |
| D714,452 S | 9/2014 | Koski et al. |
| D717,442 S | 11/2014 | Kaib et al. |
| 2003/0120311 A1 | 6/2003 | Hansen |
| 2006/0142805 A1 | 6/2006 | Katzman et al. |
| 2010/0241181 A1 | 9/2010 | Savage et al. |
| 2010/0326967 A1 | 12/2010 | Freitag et al. |
| 2011/0022105 A9 | 1/2011 | Owen et al. |
| 2012/0011382 A1 | 1/2012 | Volpe et al. |
| 2012/0158075 A1 | 6/2012 | Kaib et al. |
| 2013/0300267 A1* | 11/2013 | Richardson ........... G06F 1/1626 312/223.1 |

\* cited by examiner

EXTERNAL CASE FOR A WEARABLE MEDICAL DEVICE

CROSS REFERENCE TO RELATED APPLICATION

This application claims priority to U.S. Provisional Patent Application No. 62/082,365 filed on Nov. 20, 2014, the disclosure of which is hereby incorporated by reference in its entirety.

BACKGROUND OF THE INVENTION

Field of the Invention

The present disclosure relates generally to a case or enclosure for a portable wearable medical device, such as a wearable defibrillator, and specifically to a multi-part removable case.

Description of Related Art

Technology is available for correcting excessively slow heart rates (bradycardia) using implantable devices, commonly referred to as pacemakers, which deliver micro joule electrical pulses to a slowly beating heart in order to speed the heart rate up to an acceptable level. Also, it is well known to deliver high energy shocks (e.g., 180 to 360 joules) via external paddles applied to the chest wall in order to correct excessively fast heart rates, and prevent the possible fatal outcome of ventricular fibrillation or certain ventricular tachycardia. Bradycardia, ventricular fibrillation, and ventricular tachycardia are all electrical malfunctions (arrhythmias) of the heart. Each may lead to death within minutes unless corrected by the appropriate electrical stimulation.

One of the most deadly forms of heart arrhythmias is ventricular fibrillation, which occurs when the normal, regular electrical impulses are replaced by irregular and rapid impulses, causing the heart muscle to stop normal contractions and to begin to quiver. Normal blood flow ceases, and organ damage or death may result in minutes if normal heart contractions are not restored. Although frequently not noticeable to the victim, ventricular fibrillation is often preceded by ventricular tachycardia, which is a regular but fast rhythm of the heart. Because the victim has no noticeable warning of the impending fibrillation, death often occurs before the necessary medical assistance can arrive.

Because time delays in applying the corrective electrical treatment may result in death, implantable pacemakers and defibrillators have significantly improved the ability to treat these otherwise life-threatening conditions. Being implanted within the patient, the device continuously monitors the patient's heart for treatable arrhythmias and, when such is detected, the device applies corrective electrical pulses directly to the heart.

Normal heart function often can be restored to a person suffering ventricular fibrillation or ventricular tachycardia by a procedure known as cardioversion, the synchronized application of electrical therapy to the heart muscle. Pacemakers and defibrillators that apply corrective electrical pulses externally to the patient's chest wall also are used to correct such life-threatening arrhythmias, but suffer from a drawback insofar as it may not be possible to apply the device in time during an acute arrhythmic emergency to save the patient's life. Such treatment is needed within a few minutes to be effective.

Consequently, when a patient is deemed at high risk of death from such arrhythmias, electrical devices often are implanted so as to be readily available when treatment is needed. However, patients that have recently had a heart attack or are awaiting such an implantable device may be kept in a hospital where corrective electrical therapy is generally close at hand. Long-term hospitalization is frequently impractical due to its high cost, or due to the need for patients to engage in normal daily activities.

Wearable defibrillators have been developed for patients that have recently experienced cardiac arrest, that are susceptible to heart arrhythmias and are at temporary risk of sudden death, and that are awaiting an implantable device. However, some wearable defibrillators may lack the desired combination of size and durability to provide maximum comfort and usability to the patient.

Accordingly, a need exists for a housing for a portable, wearable defibrillator that is extremely durable to inhibit damage to the defibrillator device even if dropped or otherwise subjected to an impact. In addition, the wearable defibrillator housing should include structure for locking the housing to the device and to prevent a user from inadvertently removing the housing.

SUMMARY OF THE INVENTION

According to an aspect of the invention, a case for a wearable medical device is provided. The wearable medical device comprises internal circuitry enclosed within an external housing. The case comprises a first part sized to surround a first portion of the external housing and a second part sized to surround a second portion of the external housing. The first part comprises an inner surface with contours configured to receive corresponding contours of the external housing. The second part comprises an inner surface having contours configured to receive corresponding contours of the external housing. The first part is connected to the second part to form a parting line around the external housing.

According to another aspect of the invention, an assembly is provided. The assembly comprises a wearable medical device and a case for the wearable medical device. The wearable medical device comprises an external housing enclosing internal electronic circuitry. The case comprises a first part sized to surround a first portion of the external housing and a second part sized to surround a second portion of the external housing. The first part comprises an inner surface with contours configured to receive corresponding contours of the external housing. The second part comprises an inner surface having contours configured to receive corresponding contours of the external housing. The first part is connected to the second part to form a parting line around the external housing.

According to another aspect of the invention, a tool for removing a case from a wearable medical device is provided. The tool comprises: a body; a recess extending from a front surface of the body, which is sized and shaped to receive a portion of the wearable medical device and the case attached thereto; and one or more releasing protrusions extending from the front surface of the body positioned to contact corresponding locking protrusions extending from a portion of the wearable medical device. The releasing protrusions are configured such that upon contact with the locking protrusions, the locking protrusions are released from a protrusion receiving portion on the case, thereby releasing a first part of the case from a second part of the case. Once the first part is released from the second part, the first part can be removed from the second part by sliding the first part and the second part away from each other.

Preferred and non-limiting aspects or embodiments of the present invention will now be described in the following numbered clauses:

Clause 1: A case for a controller of a wearable medical device includes internal circuitry enclosed within an external housing. The case includes: a first part sized to surround a first portion of the external housing, the first part comprising an inner surface with contours configured to receive corresponding contours of the external housing; and a second part sized to surround a second portion of the external housing, the second part comprising an inner surface having contours configured to receive corresponding contours of the external housing. The first part can be connected to the second part to form a parting line around the external housing.

Clause 2: The case of clause 1, wherein the parting line between the first part and the second part can be flush with at least a portion of an outer surface of the first part and the second part.

Clause 3: The case of clause 1, wherein the first part can be connected to the second part by one or more of: an adhesive, ultrasonic welding, one or more fasteners, and a snap mechanism.

Clause 4: The case of clause 1, wherein the first part can be connected to the second part by slidably inserting the first part and the second part together, such that a portion of the first part overlaps a portion of the second part.

Clause 5: The case of clause 1, wherein the external housing can comprise a top cover, a front cover, and a rear cover.

Clause 6: The case of clause 5, wherein the first part can comprise a top configured to cover at least a portion of the top cover of the external housing and sides configured to cover portions of the front cover and the rear cover of the external housing.

Clause 7: The case of clause 5, wherein the second part can comprise a bottom and sides extending therefrom. The bottom and sides can be configured to cover portions of the front cover and the rear cover.

Clause 8: The case of clause 1, further comprising at least one case opening defined by the first part and/or the second part.

Clause 9: The case of clause 8, wherein the at least one opening can be positioned over one or more of a speaker, a microphone, and a response button of the controller.

Clause 10: The case of clause 8, wherein the at least one opening can allow access to the controller for electrically coupling a sensing device and/or a therapeutic device to the controller.

Clause 11: The case of clause 4, wherein the overlapping portion of the first part or the overlapping portion of the second part can comprise a sealing structure that forms a waterproof connection between the first part and the second part along the parting line.

Clause 12: The case of clause 1, wherein, when the first part is connected to the second part, the case can be waterproof.

Clause 13: The case of clause 4, wherein the overlapping portions of the first part and the second part can form a frictional engagement for securing the first part to the second part.

Clause 14: The case of clause 1, wherein the at least one case opening can comprise a battery well opening, the battery well opening being positioned at an extended side of the first part and corresponding in size and shape to a battery well of the controller.

Clause 15: The case of clause 14, wherein the parting line between the first part and the second part can be a jogged parting line positioned to accommodate the battery well opening.

Clause 16: The case of clause 1, wherein the first part and/or the second part can further comprise at least one tab extending therefrom, the tab comprising an anchor hole for securing a carrying strap to the case.

Clause 17: The case of clause 1, wherein the first part can comprise a first tab and the second part comprises a second tab. The first tab and the second tab can each comprise an anchor hole. When the first part is connected to the second part, the anchor hole of the first tab can align with at least a portion of the anchor hole of the second tab.

Clause 18: The case of clause 17, wherein the first tab or the second tab can comprise a protrusion, and wherein the protrusion can be received in a corresponding protrusion receiving portion of the first tab or the second tab.

Clause 19: The case of clause 17, wherein the first tab or the second tab can comprise a biasing member configured to bias the protrusion into the protrusion receiving portion when the first part is connected to the second part.

Clause 20: The case of clause 16, wherein the first tab can comprise a bottom lip and wherein, when the first part is connected to the second part, a bottom surface of the second tab can be received by the bottom lip.

Clause 21: The case of clause 1, wherein the controller can comprise a controller for a wearable defibrillator.

Clause 22: An assembly includes a controller for a wearable medical device and a case for the controller. The controller can include an external housing enclosing internal electronic circuitry. The case can include: a first part sized to surround a first portion of the external housing, the first part comprising an inner surface with contours configured to receive corresponding contours of the external housing; and a second part sized to surround a second portion of the external housing and comprising an inner surface having contours configured to receive corresponding contours of the external housing. The first part can be connected to the second part to form a parting line around the external housing.

Clause 23: The assembly of clause 22, wherein the controller of the wearable medical device can further comprise a battery well for attaching a battery to the external housing.

Clause 24: The assembly of clause 23, wherein, when the first part is connected to the second part, the case can comprise a case opening positioned to permit a user to access the battery well of the controller.

Clause 25: The assembly of clause 22, wherein, when the first part is connected to the second part, the case can comprise an opening configured to allow a user to access a user interface of the controller.

Clause 26: The assembly of clause 22, wherein the first part of the case can comprise a first tab and the second part of the case can comprise a second tab. The first tab and the second tab can each comprise an anchor hole. When the first part is connected to the second part, the anchor hole of the first tab can align with at least a portion of the anchor hole of the second tab.

Clause 27: The assembly of clause 26, further comprising a carrying strap. The carrying strap can be connected to the case with fasteners connected to the anchor holes of the first tab and the second tab.

Clause 28: The assembly of clause 22, wherein the controller can further comprise a wireless receiver configured to wirelessly receive data from an external sensing device and/or therapeutic device.

Clause 29: The assembly of clause 22, wherein the first part of the case can be connected to the second part of the case by slidably inserting the first part and the second part together, such that a portion of the first part overlaps a portion of the second part.

Clause 30: The assembly of clause 22, further comprising a wearable defibrillator operatively connected to the controller.

Clause 31: A tool for removing a case from a controller of a wearable medical device includes: a body; a recess extending from a front surface of the body, which is sized and shaped to receive a portion of the controller and the case attached thereto; and one or more releasing protrusions extending from the front surface of the body positioned to contact corresponding locking protrusions extending from a portion of the controller The releasing protrusions can be configured such that upon contact with the locking protrusions, the locking protrusions are released from a protrusion receiving portion on the case, thereby releasing a first part of the case from a second part of the case, such that the first part can be removed from the second part by sliding the first part and the second part away from each other.

Clause 32: The tool of clause 31, further comprising guiding structures for guiding a portion of the first part or the second part to the releasing protrusions and for aligning the releasing protrusions to locking protrusions of the case.

Clause 33: A case for a controller of a medical device having circuitry enclosed within an external housing includes: at least one part sized to surround one or more portions of the controller and comprising contours configured to receive corresponding contours of the external housing of the controller. The at least one part comprises at least one opening positioned to permit a user to access a user interface of the controller.

Clause 34: The case of clause 33, wherein the at least one part can comprise an outer surface comprising contours and protrusions shaped to resemble contours and protrusions of the external housing of the controller.

Clause 35: The case of clause 33, wherein the at least one part can be at least partially secured to the external housing of the controller.

Clause 36: The case of clause 33 comprising a protective case.

Clause 37: The case of clause 33, wherein the controller can comprise an input component, and wherein the opening is positioned to allow the user to manipulate at least a portion of the input component.

Clause 38: The case of clause 37, wherein the input component can comprise one or more of: a response button, a data entry accessory, a keypad, a trackpad, an audio input device, and/or a touch screen.

Clause 39: The case of clause 33, wherein the at least one part can comprise a first part and a second part. The first part and the second part can be configured to connect together in a tamper-proof manner.

Clause 40: The case of clause 39, wherein the first part can be connected to the second part by one or more of: an adhesive, ultrasonic welding, one or more fasteners, and a snap mechanism.

Clause 41: The case of clause 39, wherein the first part can be connected to the second part by slidably inserting the first part and the second part together, such that a portion of the first part overlaps a portion of the second part.

Clause 42: The case of clause 39, wherein the first part and/or the second part can further comprise at least one tab extending therefrom, the tab comprising an anchor hole for securing a carrying strap to the case.

Clause 43: The case of clause 39, wherein the first part can comprise a first tab and the second part can comprise a second tab. The first tab and the second tab can each comprise an anchor hole. When the first part is connected to the second part, the anchor hole of the first tab can align with at least a portion of the anchor hole of the second tab.

Clause 44: The case of clause 43, wherein one of the first tab and the second tab can comprise a protrusion. The protrusion can be received in a corresponding protrusion receiving portion of the first tab or the second tab.

Clause 45: The case of clause 33, wherein the case can be removable and replaceable, such that when the controller is provided with a replacement case, the controller appears to be in a like-new condition.

Clause 46: The case of clause 33, wherein an appearance of the case can be selected to correspond to an appearance of the external housing of the controller.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

DESCRIPTION OF THE INVENTION

Figure 1:
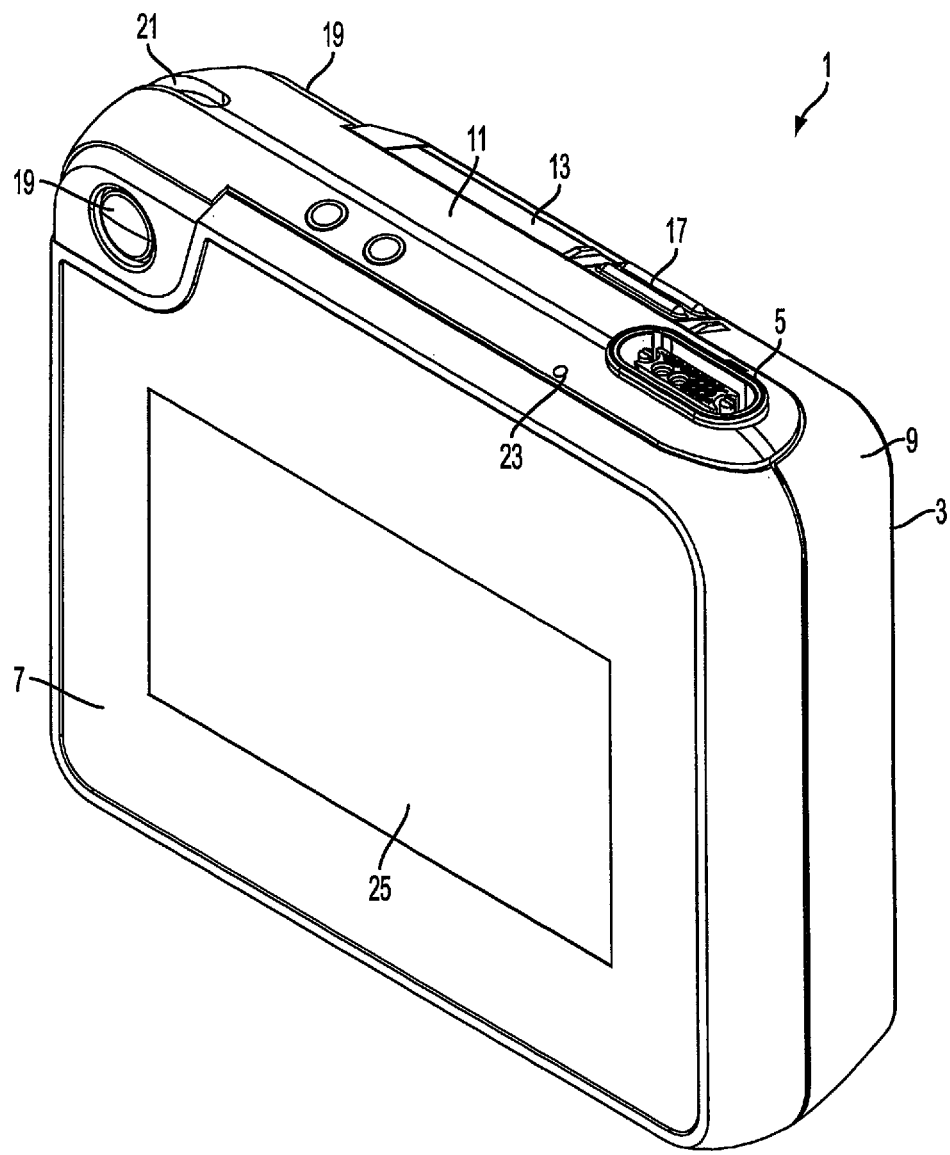
FIG. 1 is a front perspective view of a wearable defibrillator in accordance with the present invention.

As used herein, the singular form of "a", "an", and "the" include plural referents unless the context clearly dictates otherwise. For the purposes of this specification, unless otherwise indicated, all numbers expressing quantities of ingredients, reaction conditions, dimensions, physical characteristics, and so forth used in the specification and claims are to be understood as being modified in all instances by the term "about."

As used herein, the terms "right", "left", "top", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. Also, it should be understood that any numerical range recited herein is intended to include all subranges subsumed therein. For example, a range of "1 to 10" is intended to include any and all subranges between and including the recited minimum value of 1 and the recited maximum value of 10, that is, all subranges beginning with a minimum value equal to or greater than 1 and ending with a maximum value equal to or less than 10, and all subranges in between, e.g., 1 to 6.3, or 5.5 to 10, or 2.7 to 6.1.

Aspects of the present disclosure are directed to cases, covers, enclosures, and housings for a medical device and/or a controller for a medical device. In some examples, the medical device comprises an external housing enclosing internal circuitry, such as monitoring and processing circuitry. The case includes at least one part sized to surround one or more portions of the external housing of the medical device and/or controller. The case can be secured to the external housing in a tamper-proof manner. The case can be a protective case for at least a portion of the external housing of the medical device and/or controller. For example, the protective case can be configured to protect the medical device and/or controller from wear and tear experienced during normal daily use of the device. Accordingly, the protective case can protect the external housing of the medical device and/or housing of the controller from scratches, scuff marks, scrapes, dents, and other signs of use and/or of the age of the device.

In some examples, the part comprises contours configured to receive corresponding contours of the external housing of the medical device and/or controller. In one implementation, the case is configured to appear to be part of the medical device and/or controller, such that an observer (e.g., a user of the device) is unable to readily perceive that the case is independent and separable from the external housing. In this regard, users may perceive that the case is part of the external housing of the medical device and/or controller and was connected thereto at the time of manufacture. However, in some examples, the case may be removed and replaced to refurbish the medical device. Once provided with a new case, the medical device and/or controller is in a like-new condition. In some examples, the case can be disposable.

Wearable Defibrillator

Figure 2:
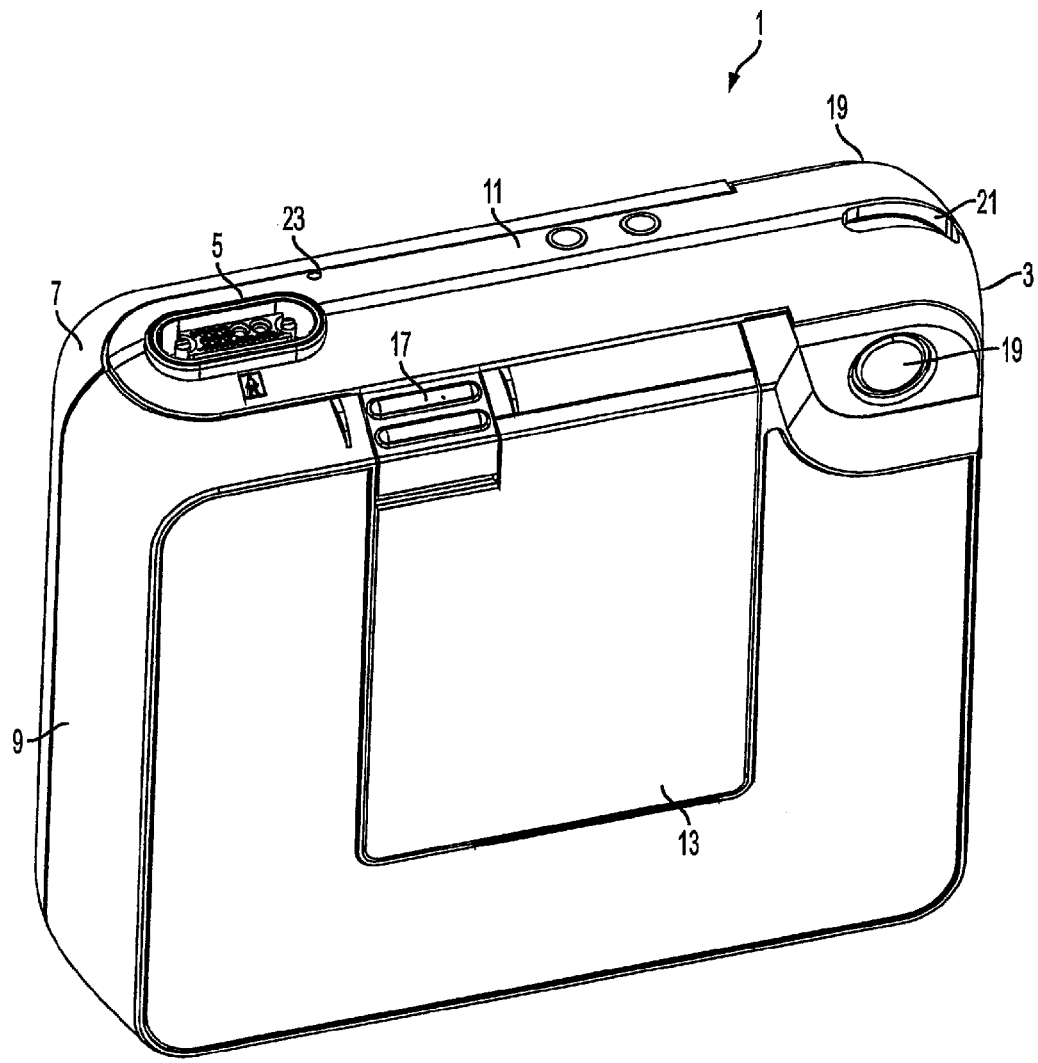
FIG. 2 is a rear perspective view of the wearable defibrillator of FIG. 1.
Figure 3:
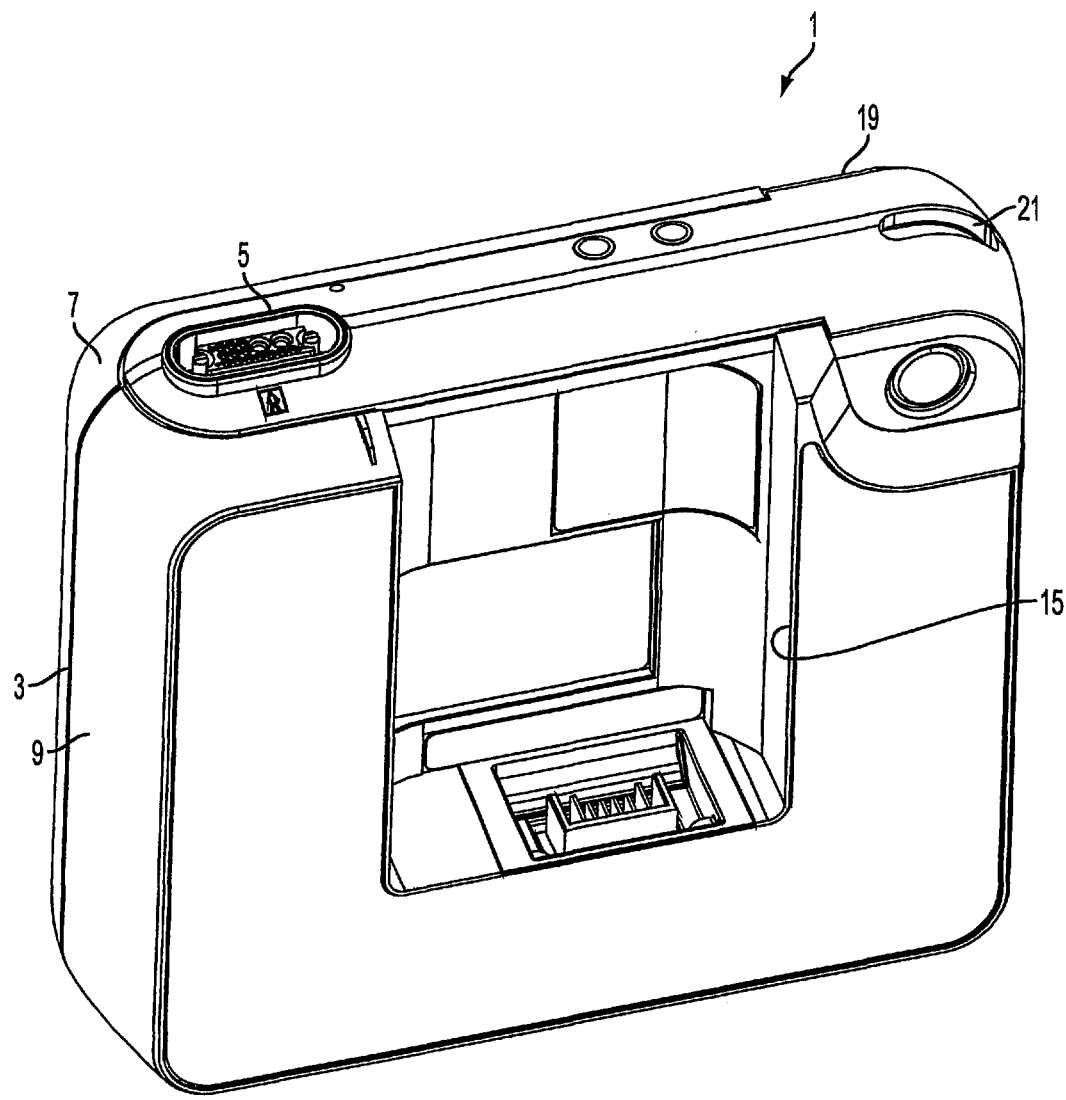
FIG. 3 is a rear perspective view of the wearable defibrillator of FIG. 1 with a battery removed.

With reference to FIGS. 1-3, a controller for a wearable medical device, such as a defibrillator generally denoted as reference numeral 1, is provided. The defibrillator 1 is configured to implement the critical functions of monitoring an ambulatory patient's ECG information and, when needed, administering a therapeutic shock to the patient. For example, defibrillators, such as the LifeVest® wearable defibrillator available from ZOLL® Corporation, are typically worn nearly continuously for two to three months at a time. During the period of time in which it is worn by the patient, the defibrillator needs to continuously or substantially continuously monitor the vital signs of the patient, to be user-friendly and accessible, to be as light-weight, comfortable, and portable as possible, and to be capable of delivering one or more life-saving therapeutic shocks when needed. As a result of the relatively long term use of the defibrillator, it is useful to include a protective case or cover surrounding the device to protect the device from drops or other damage to the device housing.

The defibrillator 1 comprises internal circuitry, such as a distributed printed circuit board (not shown). The printed circuit board is positioned within an external housing 3 and configured to be worn by a patient and connected to a therapeutic or treatment device, such as an upper body harness or vest that comprises ECG electrodes and therapy pads (not shown). The ECG electrodes and therapy pads of the harness or vest may be operatively coupled to the distributed printed circuit board within the external housing 3 via a port 5. Such wearable therapeutic devices are described in U.S. Pat. Nos. 4,928,690; 5,078,134; 5,741,306; 5,944,669; 6,065,154; 6,253,099; 6,280,461; 6,681,003; 8,271,082; and 8,369,944; as well as, United States Patent Application Publication No. 2012/0011382, which are assigned to the assignee of the present application and are hereby incorporated by reference in their entirety. Alternatively, the ECG electrodes and/or therapy pads may be configured to wirelessly transmit data to the distributed printed circuit board via a wireless data transmitter. For example, data recorded by the ECG sensors may be wirelessly transmitted from the ECG and/or therapeutic electrodes to a wireless antenna or receiver in the external housing 3 that is coupled to the printed circuit board.

In some embodiments, the external housing 3 of the defibrillator 1 comprises a front cover 7, a rear cover 9, and a top cover 11. A rechargeable and removable battery 13 is positioned within a slot or battery well 15 provided in the rear cover 9. The battery 13 is secured to the rear cover 9 by a battery latch 17. The battery latch 17 is positioned at the top left corner of the battery 13 to allow for the battery 13 to be removed from the external housing 3 with one rocking motion. This rocking motion increases usability for patients with decreased dexterity, such as a patient with arthritis. The battery 13 has sufficient capacity to administer one or more therapeutic shocks to the therapeutic electrodes as well as provide power to all of the internal components of the defibrillator 1. As mentioned hereinabove, the external housing 3 of the defibrillator 1 is configured to be worn by the patient and is accordingly sized such that it does not interfere with the patient's movement and activity. In some examples, the external housing 3 may have a length of about 5 to 6 inches, a height of about 4 to 5 inches, and a width of about 1 to 2 inches.

In some examples, the external housing 3 can also include one or more input components that allow a user to control and/or operate the device. For example, the external housing 3 can comprise a response mechanism, such as one or more patient response buttons 19, positioned, for example, in the top left corner of the housing 3. In some examples, the housing comprises a pair of response buttons 19. The response buttons 19 are positioned a small distance apart, desirably less than 1.5 inches. The location of the response buttons 19 and the distance between the response buttons 19 was chosen to enable patients with limited dexterity to easily and quickly operate the response buttons 19.

In some examples, the defibrillator 1 also comprises an audio system having a speaker port 21 and an audio input device, such as a microphone port 23, positioned on the external housing 3. The speaker port 21 is desirably positioned at least 2.5 inches away from the microphone port 23 to minimize feedback. In addition, the speaker port 21 and the microphone port 23 can be located on the top cover 11 of the external housing 3 in order to face the patient for better orientation and functionality. The speaker port 21 is also positioned on an upper corner of the external housing 3 and wraps from the top of the external housing 3 to a side thereof. This allows the speaker port 21 to be more difficult to block if the top of the defibrillator 1 is obstructed. The microphone port 23 and the speaker port 21 may be covered by a mesh or other suitable covering to prevent the ingress of fluid and/or particles into the external housing 3.

The external housing 3 of the defibrillator 1 also comprises a display screen 25, such as a touch screen, for providing information to a patient and for providing access to a user interface for controlling and/or for obtaining information about the status of the device. The display screen 25 provides information such as, but not limited to, time, battery life, volume, signal strength, device status, and any other useful information to the patient. In addition, the display screen 25 also allows the user to access various data regarding the defibrillator 1 such as, but not limited to, the settings of the device, data stored by the device, and various other data accumulated by the defibrillator 1. The display screen 25 further acts as a communication interface to allow the patient to send and receive data.

The display screen 25 may be any suitable capacitive touch screen device. For instance, the display screen 25 may comprise a 1.1 mm thick Dragontrail™ lens, manufactured by Asahi Glass Co. of Tokyo, JP, which supports a projected capacitive touch screen having a 4.3 inch LCD on the reverse side. A glass display may be provided to cover the entire front of the defibrillator 1, except for the response buttons 19, to provide the defibrillator 1 with a smooth, finished look and feel.

In operation, if the defibrillator 1 detects an abnormal condition, the defibrillator 1 is configured to stimulate the patient for a predetermined time period. The stimulus may be any stimulus perceptible by the patient. Examples of stimuli that the defibrillator 1 may produce include visual (via the display screen 25), audio (via the speaker port 21), tactile stimulation (via a vibrator (not shown) device included in the therapeutic device) or a mild stimulating alarm shock (via the therapeutic device). The one or more response buttons 19 are provided to allow a user to turn off the stimulus by pressing one or more of the response buttons 19 within the predetermined time period. For example, if the defibrillator 1 includes a pair of response buttons 19, the user may be required to press both of the response buttons 19 to turn off the stimulus. By pressing the one or more response buttons 19, the stimulus is ceased and no further action is taken by the defibrillator 1. If the patient does not take any action, the defibrillator 1 administers one or more therapeutic shocks to the therapeutic electrodes of the therapeutic device.

Removable Case

Figure 4:
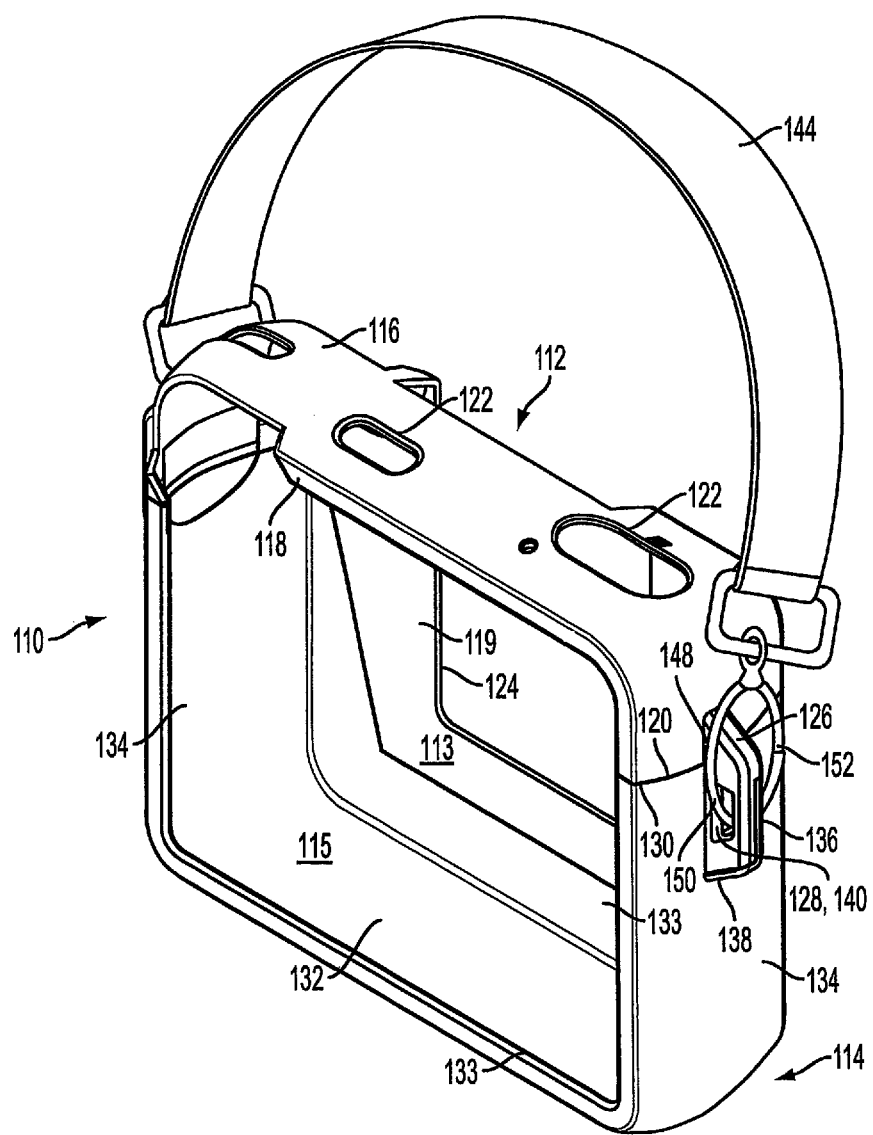
FIG. 4 is a front perspective view of a case and carrier strap for a wearable defibrillator in accordance with the present invention.
Figure 5:
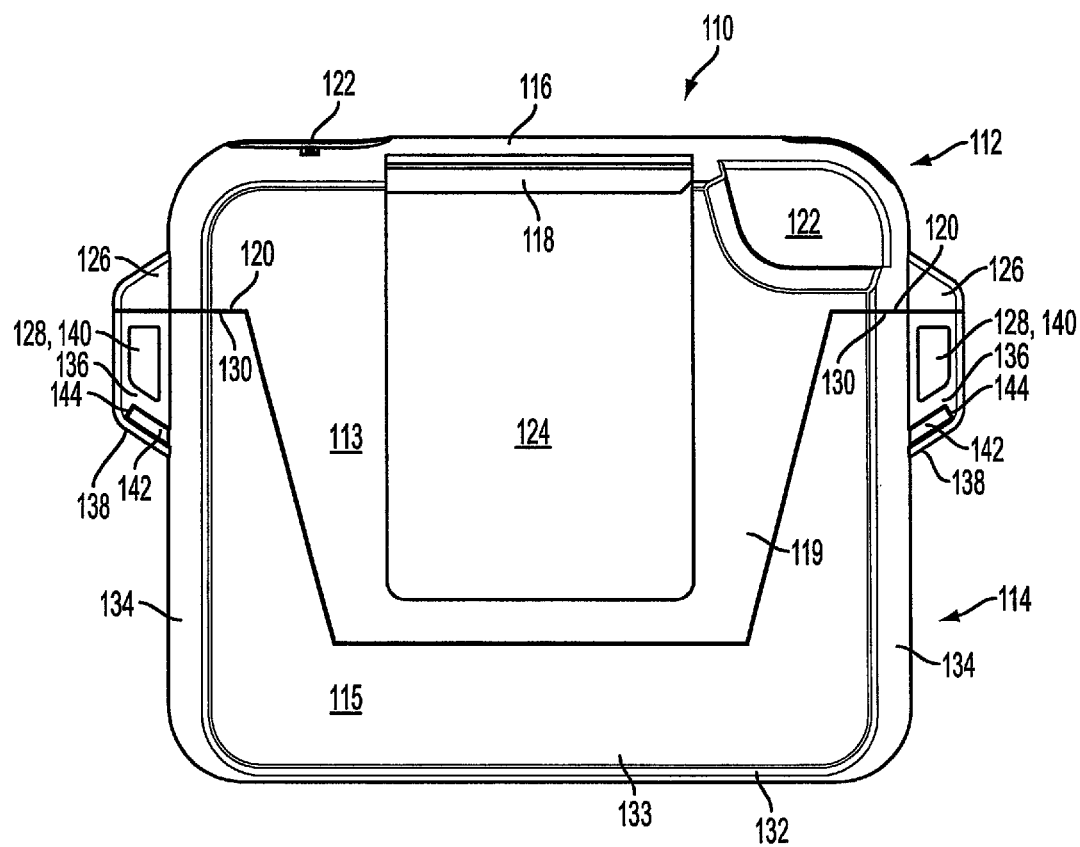
FIG. 5 is a rear view of the case of FIG. 4.
Figure 6:
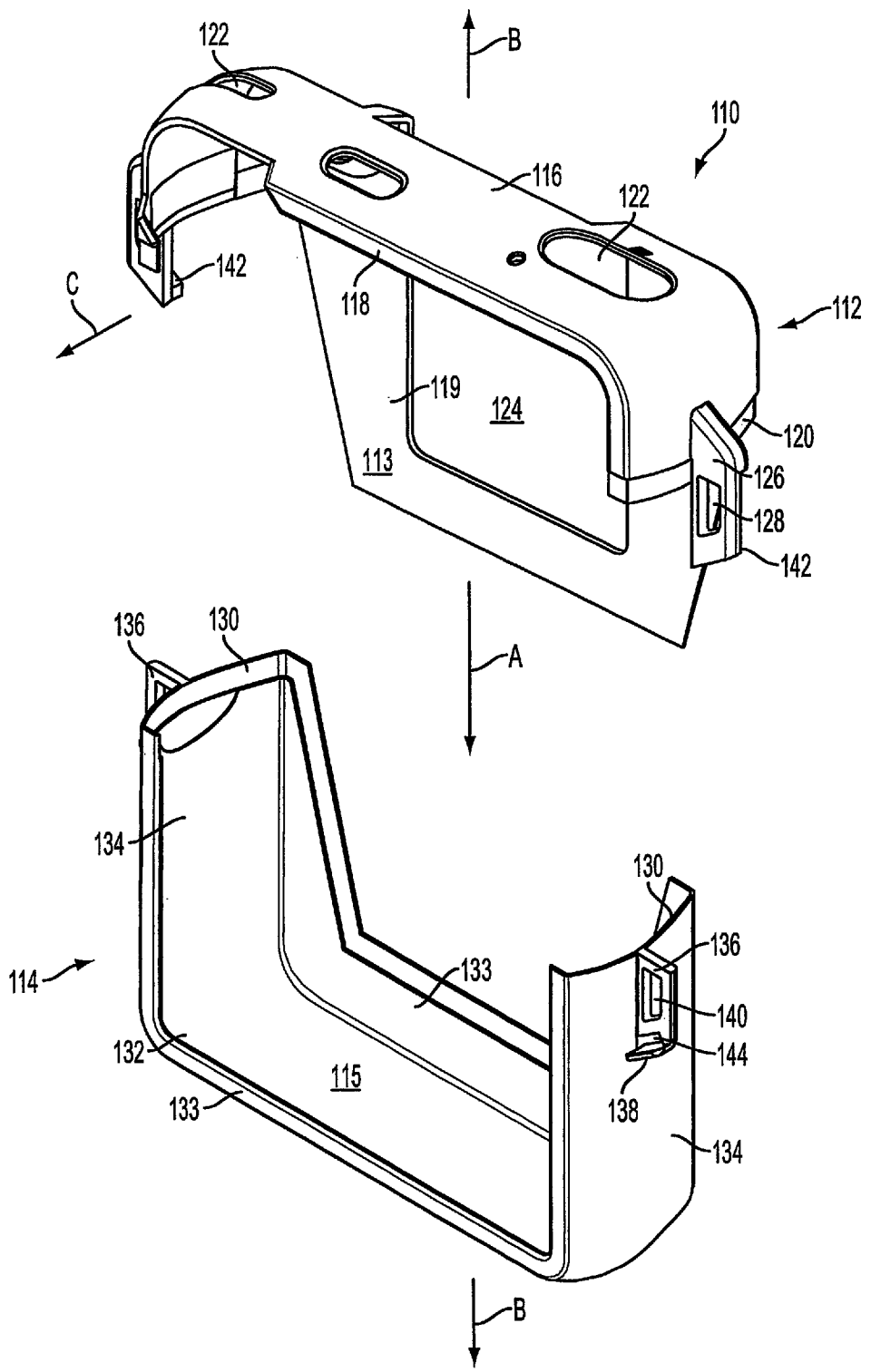
FIG. 6 is an exploded perspective view of the case of FIG. 4.

Having described the structure and operation of the defibrillator 1 and with reference to FIGS. 4-6, an exemplary external case 110, enclosure, or cover for the defibrillator 1 (shown in FIGS. 1-3) is now discussed in detail. The case 110 protects the defibrillator housing 3 (shown in FIGS. 1-3) and other external structures from damage, such as scratches or dents, which may occur during use. The case 110 is intended to be removable and replaceable, but in a non-obvious and somewhat complex manner. For example, the case 110 can include latches, connectors, and/or fasteners that join parts of the case 110 together. Removal or detachment of the latches, connectors, and/or fasteners can require a degree of manipulation or dexterity to perform. In some examples, removal or detachment of the latches, connectors, and/or fasteners can require specialized tools. Thus, the parts can be connected together in a tamper-proof manner. Accordingly, the case 110 can be removed and replaced by an authorized service technician or other party who is authorized and/or instructed to remove/replace the case 110. However, wearers generally will not attempt to remove the case 110 unless instructed to do so by a service technician for troubleshooting purposes. For example, parts of the case 110 may fit securely together giving the appearance that the case 110 is a single structure that fully encloses the defibrillator housing 3 and cannot be disconnected or removed. Similarly, the case 110 may be a shape and color that blends in with the defibrillator housing 3 creating the visual impression to an observer that the case 110 is integrally formed with the housing 3 and cannot be removed therefrom. As a result of these aesthetic elements, wearers generally should not attempt to remove the case 110 from the defibrillator ensuring that the defibrillator is securely protected at all times.

In some examples, the defibrillator 1 can be refurbished by removing an old case 110 and installing a new case. When the new case 110 is installed, the defibrillator 1 has a like-new appearance and/or is in a like-new condition. In some examples, the case 110 can be temporary and disposable. In that case, the defibrillator 1 can be provided with a new case on a regular basis.

In some examples, the case 110 may be water resistant or waterproof to protect the defibrillator 1 in a rainstorm or when the user is taking a shower or bath. In that case, the case 110 may entirely enclose the defibrillator 1 to prevent water from contacting electronic portions of the defibrillator 1. In addition, any connections between portions of the case 110 may include gaskets or other sealing structures to prevent water from flowing into an interior of the case 110. Alternatively or in addition to including a waterproof case 110, an accessory kit for protecting the defibrillator 1 and associated electronics including a waterproof enclosure may also be used. The defibrillator 1 and case 110 can be temporarily sealed in the waterproof enclosure when needed to protect the defibrillator 1. An exemplary accessory kit including a waterproof enclosure is disclosed in United States Patent Application Publication No. 2012/0158075, which is assigned to the assignee of the present application, and which is hereby incorporated by reference herein in its entirety.

With reference to FIGS. 4-6, an example of the external case 110 is illustrated. The case 110 can be at least a two part structure formed from an upper part 112 and a lower part 114, though it is recognized that, in some examples, the case 110 can include only a single part. In some examples, the parts 112, 114 are connected together (e.g., in a connected configuration as shown in FIGS. 4 and 5) by sliding the upper part 114 towards the lower part 114 in the direction A (shown in FIG. 6) about the defibrillator 1. In the connected configuration, the parts 112, 114 form an interior recess or cavity that is configured to surround and at least partially enclose the defibrillator housing 3. Accordingly, the parts 112, 114 comprise inner surfaces 113, 115 including contours, recesses, apertures, curved portions, and substantially flat surfaces that are configured to cooperate with corresponding structures of the defibrillator housing 3.

In other embodiments, the parts 112, 114 may be removably or non-removably connected together in another manner. For example, the parts 112, 114 may be connected together with an adhesive or by an ultrasonic welding process. Similarly, an adhesive material, such as tape, may be wrapped around the case 10 to reinforce the connection between the parts 112, 114. In other embodiments, mechanical connectors, such as fasteners, screws, or snap mechanisms may be used for mounting the upper part 112 to the lower part 114. In still other embodiments, the parts 112, 114 may be connected together via a joint or hinge to form a clam shell structure, in which the upper part 112 and lower part 114 are rotated together about the hinge to enclose the defibrillator housing 3.

The parts 112, 114 may be formed from any suitable hard material, such as polypropylene (PP), polystyrene, polyethylene terephthalate, high density polyethylene, or combinations thereof. Desirably, the material is recyclable, meaning that if the case 110 is damaged, it may simply be recycled and a replacement case 110 installed. Soft cases formed from various rubberized materials and/or polymers may also be used within the scope of the present disclosure. In addition, in some embodiments, the case 110 can comprise a combination of hard and soft portions. For example, the case 110 may comprise soft portions at the edges or ends of the case 110 and hard portions along its surfaces. Furthermore, while the parts 112, 114 are referred to herein as "upper" and "lower", such directional designations are not intended to limit the scope of the disclosure in any way. For example, the case 110 may be formed from a front part connected to a back part, a right-side part connected to a left-side part, or any other suitable arrangement that, when connected together, at least partially enclose the defibrillator housing 3.

The upper part 112 is sized and shaped to surround an upper portion of the defibrillator 1 (shown in FIGS. 1-3). The term "upper portion" may refer to the upper half of the defibrillator housing 3 or some other suitable section of the housing 3. The upper part 112 comprises a top 116, as well as, a front side and a rear side 119 extending from the top 116 to a bottom edge 120. The top 116 is configured to cover at least a portion of the top cover of the defibrillator housing 3. The front side covers a portion of the front face of the defibrillator 1 and may provide an opening that frames at least a portion of the display screen. The rear side 119 may comprise an extended portion having an opening 124 that allows a user to access the battery well of the defibrillator housing 3. The battery opening 124 allows a user to remove or replace the battery from the defibrillator 1 without removing or detaching any portion of the case 110 from the defibrillator housing 3. The bottom edge 120 defines an open bottom of the upper part 112. The defibrillator 1 is received through the open bottom into a recess or cavity that is sized and shaped to receive the upper portion of the defibrillator housing 3.

In some examples, the top 116 and rear side 119 of the upper part 112 can include access openings or apertures 122 such as, holes, slots, or cut away portions for accommodating or allowing a user to access portions of the defibrillator. The case 110 may include any number of opening or apertures 122 based on the configuration and functionality of the defibrillator 1. For example, an opening or aperture 122 may be positioned over the speakers, microphone, and/or response buttons of the defibrillator 1. In some examples, the opening 122 can be positioned to allow a user to access the user interface of the defibrillator 1. In addition, at least one opening or aperture 122 may be positioned to allow access to the port 5 of the defibrillator 1 for electrically coupling a sensing or therapeutic device, such as the therapeutic electrodes, to the defibrillator 1.

The bottom edge 120 of the upper part 112 may comprise an overlapping portion configured to be slidably connected to a corresponding portion on a top edge 130 of the lower part 114. The overlapping portion may comprise a beveled or stepped edge that comes into contact with and slides under or over a corresponding overlapping portion of the lower part 114 creating a substantially flush surface or parting line between the parts 112, 114. The substantially flush surface or parting line is more difficult for an observer to see than a raised portion or ridge and, therefore, contributes to the impression that the cover is formed from a single piece.

The parting line between the upper part 112 and the lower part 114 may have several shapes or orientations. In a simplest embodiment, the parting line is merely a straight line extending around the defibrillator housing 3 at a suitable position or orientation. Alternatively, as shown in FIGS. 4-6, the upper part 112 comprises the extended rear section 119 that forms a jogged parting line between the extended rear section 119 and a corresponding recessed portion on the rear side of the lower part 114. Forming the upper part 112 and lower part 114 with a jogged parting line improves the structural integrity of the lower part 114. Particularly, with the jogged parting line, the front and rear sides of the lower part 114 are substantially symmetrical meaning that the lower part 114 includes fewer extended, flexible, or flimsy portions that may bend or deform when exposed to certain forces.

In water resistant or waterproof embodiments of the case 110, the parting line between the upper part 112 and the lower part 114 may include a gasket or sealing structure for creating a watertight connection between the upper part 112 and the lower part 114. For example, the overlapping portion of the upper part 112 or the lower part 114 may include an elastomeric seal that, when pressed against a corresponding overlapping section of the other part, prevents water and other fluids from entering the interior recess of the case 110. In addition, in order to prevent water from entering the interior recess or cavity of the case 110, the case 110 may be entirely free from any sort of openings or apertures.

The upper part 112 further comprises a locking or latching mechanism to assist in securing the upper part 112 to the lower part 114 and to provide an anchor or connecting portion for attaching the case 110 to a carrier strap 146 (shown in FIG. 4), such as a lanyard or belt. For example, the upper part 112 may comprise one or more outwardly extending tabs, referred to hereinafter as upper tabs 126. The upper tabs 126 may be arranged on any suitable portion of the upper part 112. For example, the upper tabs 126 may be positioned near to or extending below the bottom edge 120 of the upper part 112 so that, when the upper part 114 and the lower part 114 are connected together, the upper tabs 126 engage a portion of the lower part 114. The upper tabs 126 may comprise an anchor hole 128 or slot. The anchor hole 128 may be configured to receive a fastener or clip for attaching the case 110 to the carrier strap 146.

In some examples, the upper part 112 comprises two upper tabs 126 positioned on opposite sides of the upper part 112. When the upper tabs 126 are positioned in this manner, the upper part 112 has a symmetrical appearance relative to a latitudinal axis of the upper part 112. Including symmetrically oriented tabs 126 allows the defibrillator 1 to hang in a stable position when being held by the carrier strap 146 attached thereto.

With continued reference to FIGS. 4-6, the lower part 114 is sized and shaped to surround a lower portion of the defibrillator 1 (shown in FIGS. 1-3). The term "lower portion" may refer to the bottom half of the defibrillator housing 3 or some other suitable section of the housing 3. The lower part 114 comprises a bottom 132, extended right and left sides 134 extending from the bottom 132, and lower front and back sides 133 configured to cover a portion of the front and rear covers of the defibrillator housing 3. The sides, 133, 134 extend from the bottom 132 to the top edge 130. The top edge 130 defines an open top of the lower part 114. The defibrillator 1 is received through the open top into a recess that is sized and shaped to receive the lower portion of the defibrillator housing. The lower part 114 may be formed from the same material as the upper part 112 to ensure that the upper and lower parts 112, 114 have a similar appearance. Alternatively, the lower part 114 may be formed from a harder, more protective, or more insulating material to provide additional protection against drops or impacts.

In some embodiments, the lower part 114 further comprises tabs, referred to hereinafter as lower tabs 136, configured to align with and, optionally, engage the upper tabs 128 of the upper part 112. For example, the lower tabs 136 may comprise anchor holes 140. When the parts 112, 114 are in the connected configuration, the anchor holes 128, 140 may be configured to align with each other to form a through hole that is capable of receiving a connector or fastener for holding the carrier strap 146. In certain embodiments, a locking piece such as a pin, grommet, or clip may be inserted through the aligned anchor holes 128, 140 to provide another means for connecting the upper part 112 and the lower part 114. The lower tabs 136 may further comprise a bottom lip 138. The upper tabs 126 may be sized and shaped to be received on the bottom lip 138. The bottom lip 138 serves two purposes. First, it prevents a user from inadvertently sliding the tabs 126, 136 past one another, thereby ensuring that the anchor holes 128, 140 and other locking structures are properly aligned. Second, the bottom lip 138 is an aesthetic feature that improves the appearance of the case 110 by contributing to the overall impression that the case 110 is formed as a single unit.

Figure 7A:
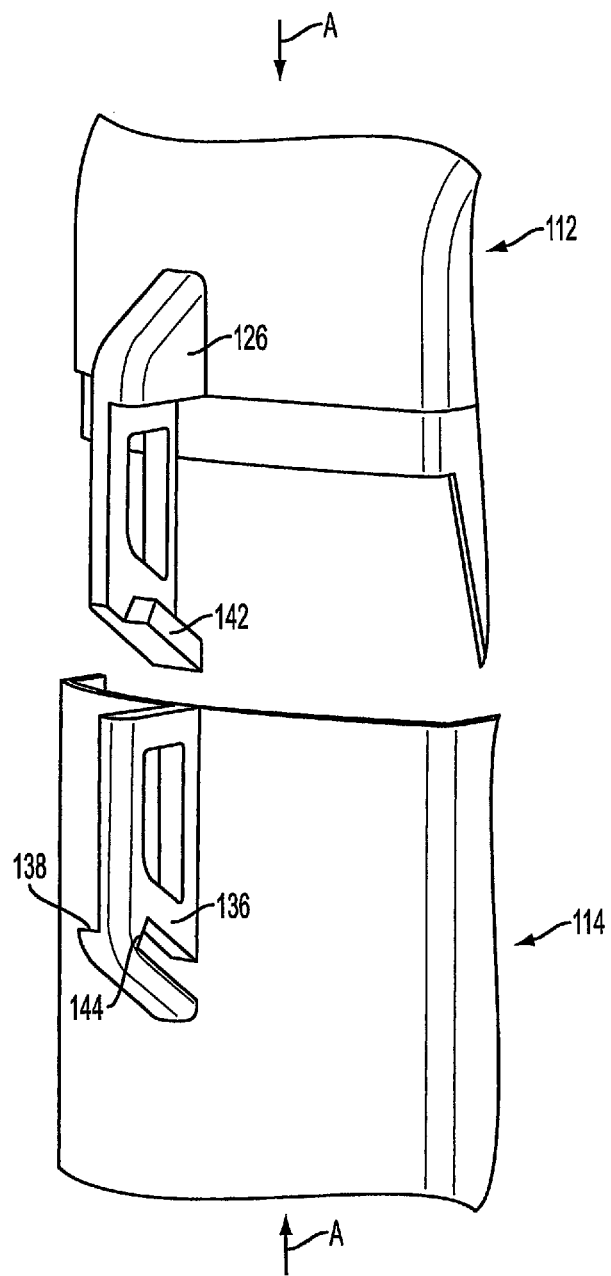
FIG. 7A is a perspective view of a portion of the case of FIG. 4 in a disconnected configuration.
Figure 7B:
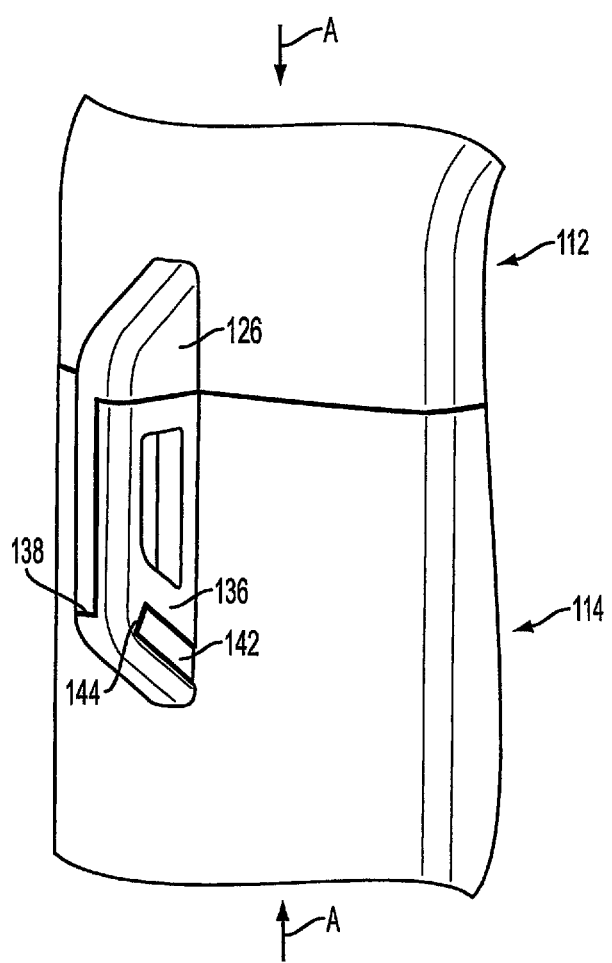
FIG. 7B is a perspective view of a portion of the case of FIG. 4 in a connected configuration.

With reference to FIGS. 7A and 7B, the upper tabs 126 and lower tabs 136 may further comprise an additional locking or latching structure for further securing the parts 112, 114 in the connected configuration. For example, the upper tabs 136 may comprise a protrusion 142, such as a detent, ridge, bulge, shelf, or post positioned to be inserted through a corresponding protrusion receiving portion in the lower tab 136, such as a latch hole 144. The latch hole 144 is sized and shaped to receive the protrusion 142. For example, if the protrusion 142 is a post or detent having a circular cross section, then the latch hole 144 has a circular cross section. If the protrusion 142 is a square or rectangular shaped shelf or ridge, the corresponding hole 144 is a square or rectangular shaped hole sized to receive a portion of the shelf or ridge.

In operation, as the parts 112, 114 slide together, a portion of the lower tab 136 contacts the protrusion 142 of the upper tab 126 which biases the upper tab 126 away from the lower tab 136. Continued movement in the direction A causes the protrusion 142 to slide along a sidewall or surface of the lower tab 136 and, when in an appropriate position, to snap into the latch hole 144 to connect the upper tab 126 to the lower tab 136. In this position, a bottom surface of the upper tab 126 rests against the bottom lip 138 of the lower tab 136.

Carrier Strap

With specific reference to FIG. 4, the carrier strap 146 is an elongated piece of synthetic or natural material that can be worn over a patient's shoulder or around his or her waist for carrying the defibrillator 1. Fasteners or hangers, such as clips 148, are attached to the ends of the carrier strap 146. The clips 148 may be c-shaped clips 148 having a c-shaped body 150 and a pivoting member 152 that is biased to a closed position to form a closed ring. When the parts 112, 114 are in the connected configuration, the clips 148 can be inserted through the aligned anchor holes 128, 140 of the tabs 126, 136. Thus, the clips 148 are another mechanism for securing the upper part 112 and the lower part 114 of the case 110 together and for reducing the likelihood that a wearer will inadvertently detach the parts 112, 114. Particularly, the clips 148 lock the upper part 112 and the lower part 114 in place, thereby preventing the wearer from sliding the upper part 112 away from the lower part 114. In this way, even if the engagement between the bottom edge 120 and top edge 130 of the parts 112, 114 or between the protrusion 142 and latch hole 144 is overcome by force, the clip 148 will still hold the case 110 together. To remove the case 110 from the defibrillator 1, the wearer must first remove the clips 148 from the anchor holes 128, 140 before sliding the parts 112, 114 apart in direction B (shown in FIG. 6).

Connecting and Disconnecting the Case from the Defibrillator

With reference again to FIGS. 4-6 and having described the structure of the wearable defibrillator 1 (shown in FIGS. 1-3) and case 110, steps for securing the case 110 around the defibrillator housing 3 will now be discussed in detail. A user, such as a technician, physician, or patient to be monitored, begins by placing the upper part 112 and lower part 114 of the case over corresponding portions of the wearable defibrillator 1. The user then slides the upper part 112 and the lower part 114 toward one another in direction A (shown in FIG. 6) causing the bottom edge 120 of the upper part 112 to slightly overlap the top edge 130 of the lower part 114. Continuing to push the upper part 112 and the lower part 114 toward one another causes the tabs 126, 136 to slide together, thereby causing the protrusion 142 to insert through the corresponding latch hole 144 to form a suitable connection therewith. In this connected configuration, the bottom surface of the upper tab 126 contacts and rests against the lip 138 extending from the lower tab 136. Once the upper part 112 and the lower part 114 are suitably secured together, the user inserts a portion of the lanyard clip 148 through the aligned holes 128, 140 and releases the pivoting member 152 of the clip 148 allowing it to lock in place. In this way, the carrier strap 146 is securely connected to the case 110. Once the carrier strap 146 is attached to the case 110, the defibrillator 1 is ready to be worn by a patient. For example, the wearer may place the carrier strap 146 over his or her shoulder or around his or her waist for easy and discreet carrying.

To remove the case 110, the user detaches the clips 148 from the anchor holes 128, 140 by depressing the pivoting member 152 of the clip 148 while removing the body 150 of the clip 148 from the anchor hole 128, 140. After the clips 148 are removed, the user separates the upper part 112 of the case 110 from the lower part 114. For example, the user may press against the protrusions 142 in a direction C (shown in FIG. 6) to release the protrusions 142 from the holes 144. Once the protrusions 142 are released, the user slides the upper part 112 away from the lower part 114 in direction B (shown in FIG. 6). In certain embodiments, the user may use a tool, such as a flat head screw driver, to depress the protrusion 142. In other embodiments, the user may press the protrusion 142 with his or her finger or finger nail.

Case Removing Tool

Figure 8:
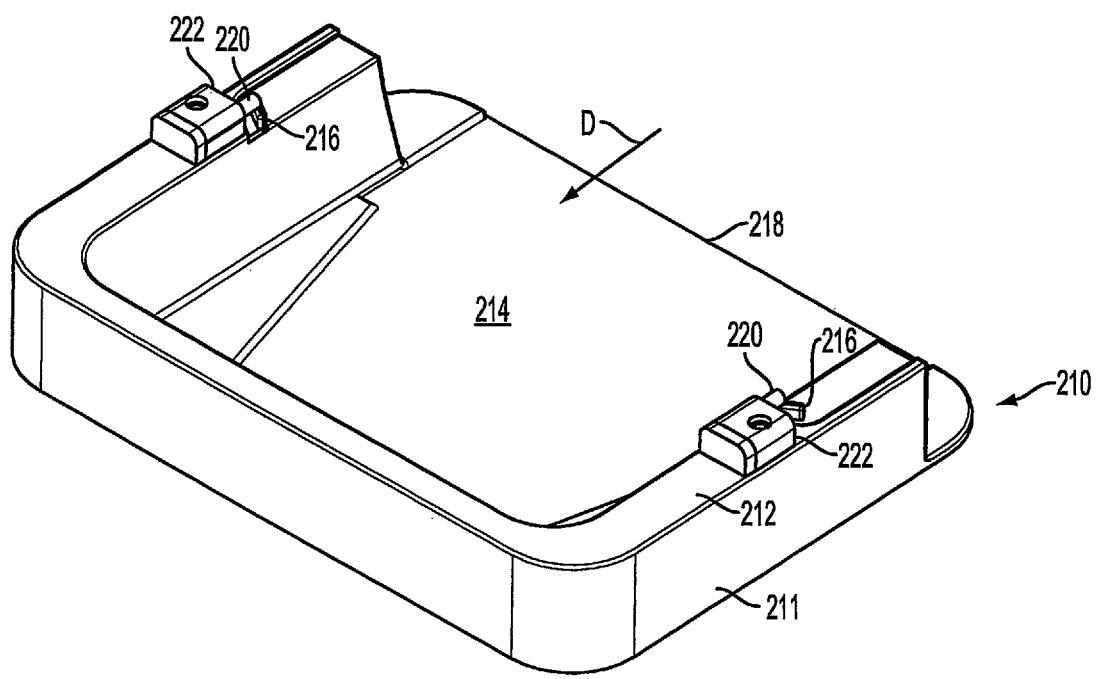
FIG. 8 is a perspective view of a case removing device for use with the case of FIG. 4.

With reference to FIG. 8, a tool 210 for removing the parts 112, 114 of the case 110 (shown in FIGS. 4-7B) from the defibrillator housing 3 is illustrated. The tool 210 comprises a body 211 comprising a front surface 212 and a recess 214 of a suitable size and shape to receive the defibrillator 1 and case 110 attached thereto. The recess 214 comprises a bottom and sidewalls including curved portions, surfaces, recesses and other structural features that are configured to receive corresponding structural features of the defibrillator 1 and case 110. A number of protrusions 216 extend from the front surface 212 of the body 211. The protrusions 216 are positioned to contact the protrusions 142 (shown in FIGS. 4-7B) extending from the upper tab 126 of the case 110 when the case 110 and defibrillator 1 are inserted in the recess. The protrusions 216 may have a sloped or beveled profile so that a user can slide the case 110 and defibrillator 1 into the recess 214 through an open top 218 in the direction of arrow D. The body 211 may further comprise structures for assisting in correctly positioning the case 110. For example, posts 220 and shelf portions 222 may extend from the front surface 212. The posts 220 and shelf portions 222 are configured to receive the tabs 126, 136 (shown in FIGS. 4-6) in a desired orientation, such that the protrusions 216 come into contact with the corresponding protrusion 142 of the upper tab 126.

To remove the case 110 from the defibrillator 1, the user slides the defibrillator 1 and attached case 110 into the recess 214 in direction D shown in FIG. 8. The tabs 126, 136 of the case 110 contact the posts 220, thereby ensuring correct positioning. Continuing to slide the case 110 in the direction D brings a bottom lip of the tab into contact with the shelf portion 222, which indicates that the protrusions 216 are properly aligned with protrusions 142 of the case 110. The user then firmly presses the defibrillator 1 into the recess 214 causing the protrusions 216 to press against the protrusions 142 extending from the upper tab 126. The contact causes the protrusions 142 to retract through the latch holes 144 of the lower tab 136. In this way, the upper tab 126 is released from the lower tab 136. Once the tabs 126, 136 are released, the user can remove the parts 112, 114 of the case 110 by sliding the upper part 112 away from the lower part 114 in the direction of arrow B (shown in FIG. 6).

Case with Biasing Tab

Figure 9A:
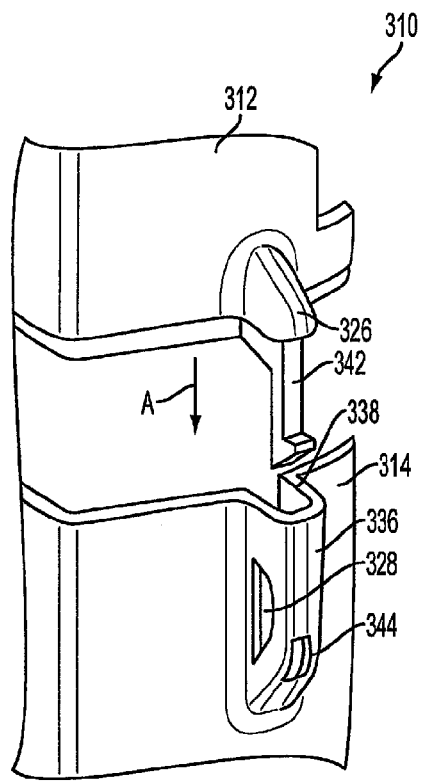
FIG. 9A is a schematic drawing of a portion of another embodiment of a case for a wearable defibrillator in a disconnected configuration, in accordance with the present invention.
Figure 9B:
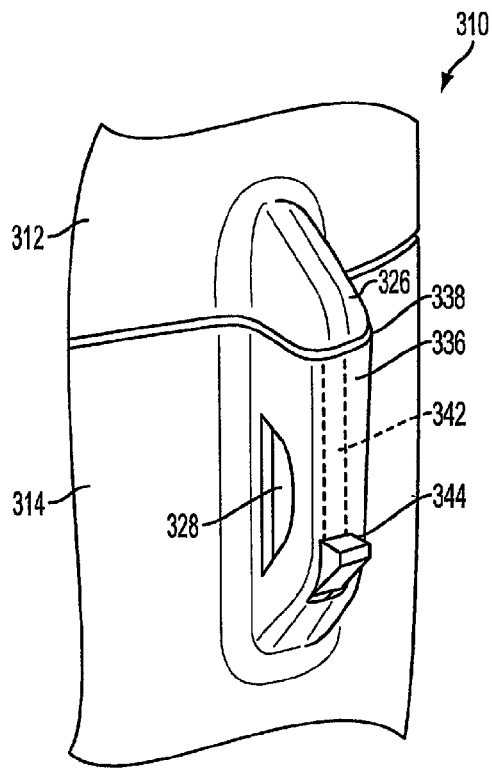
FIG. 9B is a schematic drawing of the case of FIG. 9A in a connected configuration.

With reference to FIGS. 9A and 9B, a portion of another embodiment of a case 310 for the wearable defibrillator is illustrated. The case 310 is substantially similar to the case 110 illustrated in FIGS. 4-7B, except for the structure of the tabs 326, 336 which connect the upper part 312 and the lower part 314 together. As in the previously described embodiments, the case 310 is a two part structure including the upper part 312 and the lower part 314 that are configured to slide together to form a structure that at least partially encloses the defibrillator housing 3 (shown in FIGS. 1-3). The upper tab 326 extends from an outer surface of the upper part 312. The upper tab 326 comprises a cap 325 or top portion having a biasing member 342, such as a leaf spring, extending therefrom. The lower tab 336 is a substantially cup-shaped receiving member having an open top 338 or slot for receiving the biasing member 342 of the upper tab 326. The lower tab 336 further comprises a protrusion receiving portion on a sidewall thereof, such as a latch hole 344, configured to engage an end of the biasing member 342 to form a suitable connection therewith. The lower tab 336 further comprises an anchor hole 328 for receiving a fastener or hanger connected to a carrier strap, such as the strap shown in FIG. 4. When in the connected configuration, the cap 325 of the upper tab 326 at least partially covers the open top 338 causing the tabs 326, 336 to appear to be a single structure.

In use, the user moves the upper part 312 toward the lower part 314 in the direction of arrow A (shown in FIG. 9A). Movement in the direction A inserts the biasing member 342 through the open top 338 and causes the biasing member 342 to deflect in an inward direction as a result of contact with a sidewall of the lower tab 336. Continued movement of the parts 312, 314 in direction A causes the biasing member 342 to travel in a downward direction along the sidewall of the lower tab 336 until the latch hole 344 is reached. The biasing member 342 then deflects in an outward direction into the latch hole 344, thereby connecting the upper part 312 to the lower part 314. The connection or engagement between the upper part 312 and the lower part 314 can be removed by pressing on a portion of the biasing member 342 to release it from the latch hole 344. Once the biasing member 342 is released, the user can pull the upper part 312 and the lower part 314 away from each other in direction B (shown in FIG. 9B) to disconnect the case 310 from the defibrillator 1.

Case with Locking Pin Connection

Figure 10A:
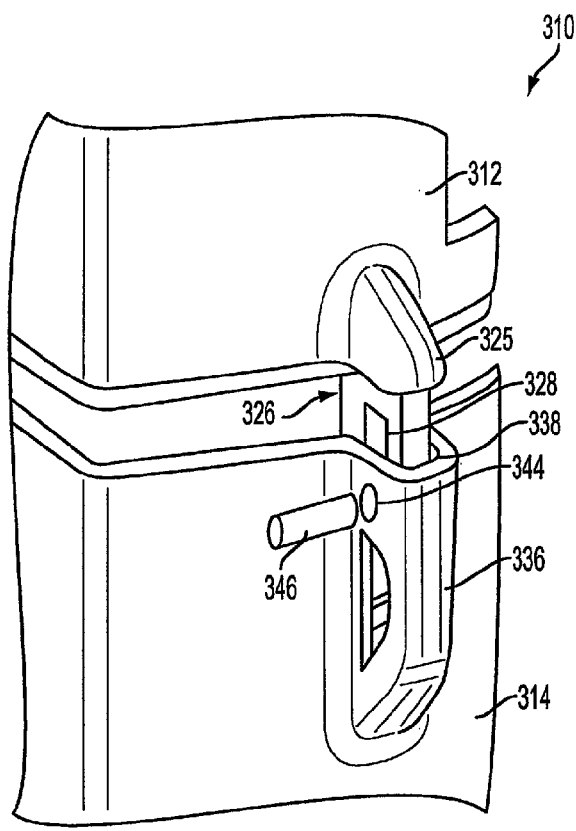
FIG. 10A is a schematic drawing of a portion of another embodiment of a case for a wearable defibrillator in a disconnected configuration, in accordance with the present invention.
Figure 10B:
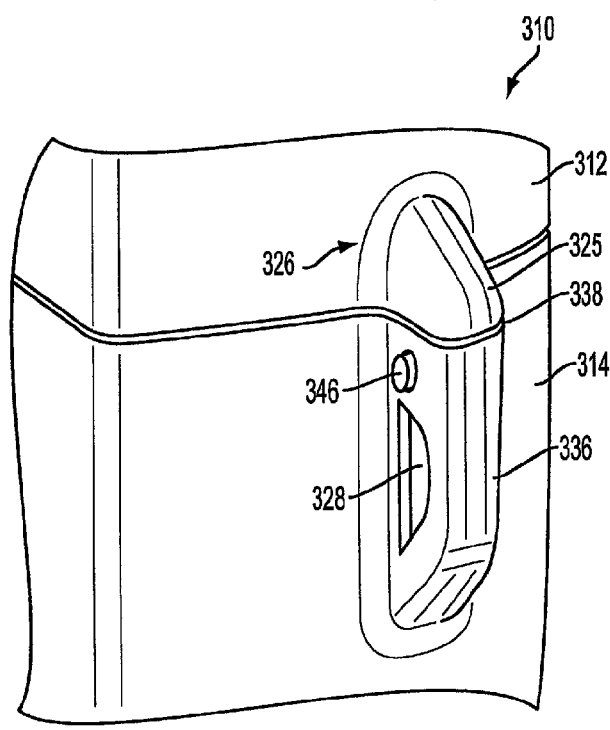
FIG. 10B is a schematic drawing of the case of FIG. 10A in a connected configuration.

With reference to FIGS. 10A and 10B, another embodiment of a portion of a case 310 for a wearable defibrillator is illustrated. As in the previously described embodiment, the case 310 is a two part structure including an upper part 312 and a lower part 314. The upper part 312 and the lower part 314 are configured to slide together to form the case 310 that surrounds or encloses at least a portion of the wearable defibrillator. As in previously described embodiments, the upper part 312 comprises upper tabs 326 and the lower part 314 comprise corresponding lower tabs 336. For example, the upper tab 326 may be a substantially flat piece configured to be received in a corresponding cup shaped lower tab 336. The upper tab 326 and lower tab 336 may comprise anchor holes 328, 340 capable of being connected to a clip or fastener for connecting the tabs 326, 336 to a carrier strap 146, such as the strap 146 shown in FIG. 4. The tabs 326, 336 further comprise a smaller latch hole 344 or fixing point that align when the tabs are connected together. The user may insert a locking member 346, such as a dial, pin, clip, or similar elongated member through the latch hole 344 to secure the upper tab 312 to the lower tab 314. To disconnect the upper part 312 from the lower part 314, the user removes the clip 348 (shown in FIG. 4) from the anchor holes 328, 340 and removes the locking member 346 from the locking hole 344. Once these items are removed, the user may slide the upper part 312 away from the lower part 314 to remove the case 310 from the defibrillator housing 3.

Front Part/Rear Part Case

Figure 11:
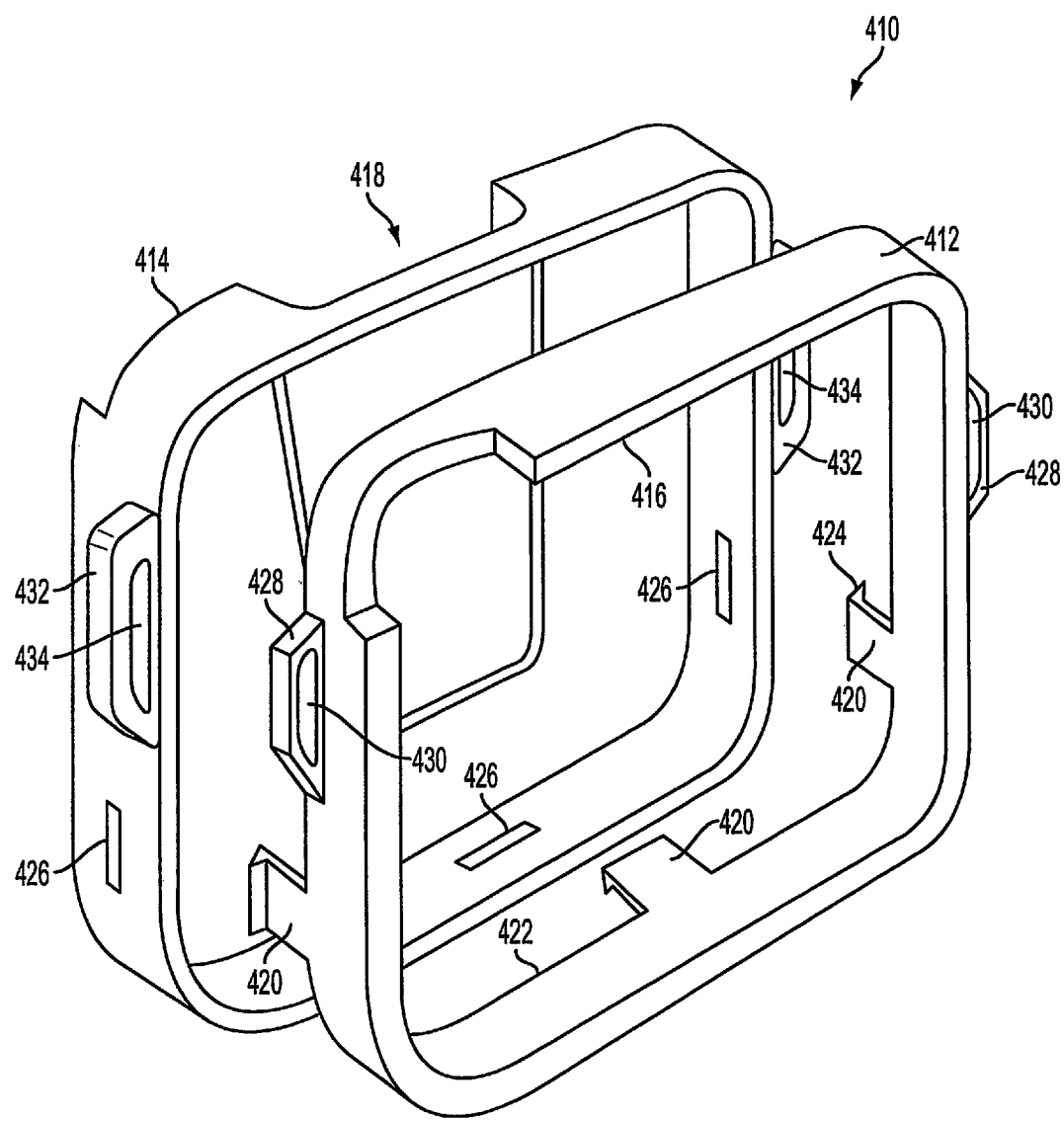
FIG. 11 is a schematic drawing of a portion of another embodiment of a case for a wearable defibrillator, in accordance with the present invention.

With reference to FIG. 11, another embodiment of a case 410 for a wearable defibrillator is illustrated. The case 410 is a two-part case including a front part 412 and a rear part 414. Once connected together, the parts 412, 414 form a case including a front opening 416 for viewing and manipulating the touchscreen of the defibrillator 1 and a rear opening 418 for accessing the battery well of the defibrillator 1. The front part 412 comprises a number of biasing members 420, such as leaf springs, extending from an inner edge 422 of the front part 412. The biasing members 420 are formed from a flexible member having a connecting structure 424, such as a bulbous portion, ridge, or shelf at one end. The rear part comprises a number of slots 426 or holes configured to receive the connecting structure 424 of the biasing member 420 to form a secure connection between the front part 412 and the rear part 414. The front part 412 also comprises a front tab 428 with an anchor hole 430. The rear part 412 comprises a rear tab 432 having a corresponding anchor hole 434. The tabs 428, 432 are positioned such that when the front part 412 and the rear part 414 are connected together, the tabs 428, 432 align so that clips can be inserted therethrough. To connect the parts 412, 414 together, the user presses the front part 412 against the rear part 414, causing the biasing members 420 to defect in an inward direction. Continued pressured causes the connecting structure 424 of the biasing member 420 to align with the slots 426 in the rear part 414 and to deflect outward into the slots 426 to lock or connect the front part 412 to the rear part 414. The user may then attach the carrying strap to the case 410 by attaching the clip or fastener through the anchor holes 430, 434. The case 410 may be removed from the defibrillator 1 by disconnected the clips from the anchor holes 430, 434 and deflecting the biasing members 420 through the slots 426. Once the biasing members 420 are released from the slots 426, the user may remove the front part 412 from the rear part 414.

Although a defibrillator 1 and case 110, 310, 410 have been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements. For example, it is to be understood that this disclosure contemplates that, to the extent possible, one or more features of any embodiment can be combined with one or more features of any other embodiment.

The invention claimed is:

1. A case for a controller of a wearable medical device, the controller comprising internal circuitry enclosed within an external housing, the case comprising:
a first part sized to surround a first portion of the external housing, the first part comprising an inner surface with contours configured to receive corresponding contours of the external housing; and
a second part sized to surround a second portion of the external housing and comprising an inner surface having contours configured to receive corresponding contours of the external housing,
wherein the first part is connected to the second part to form a parting line around the external housing, and
wherein the first part comprises a first tab and the second part comprises a second tab, wherein the first tab and the second tab each comprise an anchor hole, and wherein when the first part is connected to the second part, the anchor hole of the first tab aligns with at least a portion of the anchor hole of the second tab.

2. The case of claim 1, wherein the parting line between the first part and the second part is flush with at least a portion of an outer surface of the first part and the second part.

3. The case of claim 1, wherein the first part is connected to the second part by one or more of: an adhesive, ultrasonic welding, one or more fasteners, and a snap mechanism.

4. The case of claim 1, wherein the first part is connected to the second part by slidably inserting the first part and the second part together, such that a portion of the first part overlaps a portion of the second part.

5. The case of claim 1, wherein the external housing comprises a top cover, a front cover, and a rear cover.

6. The case of claim 5, wherein the first part comprises a top configured to cover at least a portion of the top cover of the external housing and sides configured to cover portions of the front cover and the rear cover of the external housing.

7. The case of claim 5, wherein the second part comprises a bottom and sides extending therefrom, the bottom and sides being configured to cover portions of the front cover and the rear cover.

8. The case of claim 1, further comprising at least one case opening defined by the first part and/or the second part.

9. The case of claim 8, wherein the at least one opening is positioned over one or more of a speaker, a microphone, and a response button of the controller.

10. The case of claim 8, wherein the at least one opening allows access to the controller for electrically coupling a sensing device and/or a therapeutic device to the controller.

11. The case of claim 4, wherein the overlapping portion of the first part or the overlapping portion of the second part comprises a sealing structure that forms a waterproof connection between the first part and the second part along the parting line.

12. The case of claim 1, wherein, when the first part is connected to the second part, the case is waterproof.

13. The case of claim 4, wherein the overlapping portions of the first part and the second part form a frictional engagement for securing the first part to the second part.

14. The case of claim 1, wherein the at least one case opening comprises a battery well opening, the battery well opening being positioned at an extended side of the first part and corresponding in size and shape to a battery well of the controller.

15. The case of claim 14, wherein the parting line between the first part and the second part is a jogged parting line positioned to accommodate the battery well opening.

16. The case of claim 1, wherein the first tab or the second tab comprises a protrusion, and wherein the protrusion is received in a corresponding protrusion receiving portion of the first tab or the second tab.

17. The case of claim 1, wherein the first tab or the second tab comprises a biasing member configured to bias the protrusion into the protrusion receiving portion when the first part is connected to the second part.

18. The case of claim 1, wherein the first tab comprises a bottom lip and wherein, when the first part is connected to the second part, a bottom surface of the second tab is received by the bottom lip.

19. A case for a controller of a wearable medical device, the controller comprising internal circuitry enclosed within an external housing, the case comprising:
a first part sized to surround a first portion of the external housing, the first part comprising an inner surface with contours configured to receive corresponding contours of the external housing; and
a second part sized to surround a second portion of the external housing and comprising an inner surface having contours configured to receive corresponding contours of the external housing, wherein the first part is connected to the second part to form a parting line around the external housing, and wherein the controller comprises a controller for a wearable defibrillator.

20. An assembly comprising:
a controller for a wearable medical device, the controller comprising an external housing enclosing internal electronic circuitry; and
a case for the controller, the case comprising:
   a first part sized to surround a first portion of the external housing, the first part comprising an inner surface with contours configured to receive corresponding contours of the external housing; and
   a second part sized to surround a second portion of the external housing and comprising an inner surface having contours configured to receive corresponding contours of the external housing,
wherein the first part is connected to the second part to form a parting line around the external housing, and
wherein the first part of the case comprises a first tab and the second part of the case comprises a second tab, wherein the first tab and the second tab each comprises an anchor hole, and wherein when the first part is connected to the second part, the anchor hole of the first tab aligns with at least a portion of the anchor hole of the second tab.

21. The assembly of claim 20, wherein the controller of the wearable medical device further comprises a battery well for attaching a battery to the external housing.

22. The assembly of claim 21, wherein, when the first part is connected to the second part, the case comprises a case opening positioned to permit a user to access the battery well of the controller.

23. The assembly of claim 20, wherein, when the first part is connected to the second part, the case comprises an opening configured to allow a user to access a user interface of the controller.

24. The assembly of claim 20, further comprising a carrying strap, and wherein the carrying strap is connected to the case with fasteners connected to the anchor holes of the first tab and the second tab.

25. The assembly of claim 20, wherein the controller further comprises a wireless receiver configured to wirelessly receive data from an external sensing device and/or therapeutic device.

26. The assembly of claim 20, wherein the first part of the case is connected to the second part of the case by slidably inserting the first part and the second part together, such that a portion of the first part overlaps a portion of the second part.

27. An assembly comprising:
a controller for a wearable medical device, the controller comprising an external housing enclosing internal electronic circuitry; and
a case for the controller, the case comprising:
   a first part sized to surround a first portion of the external housing, the first part comprising an inner surface with contours configured to receive corresponding contours of the external housing;
   a second part sized to surround a second portion of the external housing and comprising an inner surface having contours configured to receive corresponding contours of the external housing; and
a wearable defibrillator operatively connected to the controller,
wherein the first part is connected to the second part to form a parting line around the external housing.

28. A case for a controller of a medical device, the controller comprising circuitry enclosed within an external housing, the case comprising:
at least one part sized to surround one or more portions of the controller and comprising contours configured to receive corresponding contours of the external housing of the controller, the at least one part comprising a first part and a second part configured to connect together in a tamper-proof manner,
wherein the at least one part comprises at least one opening positioned to permit a user to access a user interface of the controller, and
wherein the first part comprises a first tab and the second part comprises a second tab, wherein the first tab and the second tab each comprise an anchor hole, and wherein when the first part is connected to the second part, the anchor hole of the first tab aligns with at least a portion of the anchor hole of the second tab.

29. The case of claim 28, wherein the at least one part comprises an outer surface comprising contours and protrusions shaped to resemble contours and protrusions of the external housing of the controller.

30. The case of claim 28, wherein the at least one part is at least partially secured to the external housing of the controller.

31. The case of claim 28 comprising a protective case.

32. The case of claim 28, wherein the controller comprises an input component, and wherein the opening is positioned to allow the user to manipulate at least a portion of the input component.

33. The case of claim 32, wherein the input component comprises one or more of a response button, a data entry accessory, a keypad, a trackpad, an audio input device, and/or a touch screen.

34. The case of claim 28, wherein the first part is connected to the second part by one or more of: an adhesive, ultrasonic welding, one or more fasteners, and a snap mechanism.

35. The case of claim 28, wherein the first part is connected to the second part by slidably inserting the first part and the second part together, such that a portion of the first part overlaps a portion of the second part.

36. The case of claim 28, wherein the first part and/or the second part further comprise at least one tab extending therefrom, the tab comprising an anchor hole for securing a carrying strap to the case.

37. The case of claim 28, wherein one of the first tab and the second tab comprise a protrusion, and wherein the protrusion is received in a corresponding protrusion receiving portion of the first tab or the second tab.

38. A case for a controller of a medical device, the controller comprising circuitry enclosed within an external housing, the case comprising:
at least one part sized to surround one or more portions of the controller and comprising contours configured to receive corresponding contours of the external housing of the controller,
wherein the at least one part comprises at least one opening positioned to permit a user to access a user interface of the controller, and
wherein the case is removable and replaceable, such that when the controller is provided with a replacement case, the controller appears to be in a like-new condition.

39. A case for a controller of a medical device, the controller comprising circuitry enclosed within an external housing, the case comprising:

at least one part sized to surround one or more portions of the controller and comprising contours configured to receive corresponding contours of the external housing of the controller, wherein the at least one part comprises at least one opening positioned to permit a user to access a user interface of the controller, and wherein an appearance of the case is selected to correspond to an appearance of the external housing of the controller.

* * * * *